US010561311B2

(12) United States Patent
Tokuyama et al.

(10) Patent No.: US 10,561,311 B2
(45) Date of Patent: Feb. 18, 2020

(54) OPHTHALMIC IMAGING APPARATUS AND OPHTHALMIC INFORMATION PROCESSING APPARATUS

(71) Applicant: TOPCON CORPORATION, Itabashi-ku, Tokyo (JP)

(72) Inventors: Takaki Tokuyama, Tokyo (JP); Katsuhiro Yamada, Tokyo (JP)

(73) Assignee: Topcon Corporation, Itabashi-ku, Tokyo (JP)

( * ) Notice: Subject to any disclaimer, the term of this patent is extended or adjusted under 35 U.S.C. 154(b) by 11 days.

(21) Appl. No.: 15/768,191

(22) PCT Filed: Oct. 12, 2016

(86) PCT No.: PCT/JP2016/080170
§ 371 (c)(1),
(2) Date: Apr. 13, 2018

(87) PCT Pub. No.: WO2017/065146
PCT Pub. Date: Apr. 20, 2017

(65) Prior Publication Data
US 2018/0303334 A1 Oct. 25, 2018

(30) Foreign Application Priority Data
Oct. 16, 2015 (JP) .................................. 2015-205049

(51) Int. Cl.
*A61B 3/00* (2006.01)
*A61B 3/10* (2006.01)
(Continued)

(52) U.S. Cl.
CPC .......... *A61B 3/0025* (2013.01); *A61B 3/0041* (2013.01); *A61B 3/102* (2013.01);
(Continued)

(58) Field of Classification Search
CPC ........... A61B 3/14; A61B 3/0025; A61B 3/12; A61B 3/102; A61B 3/0008
(Continued)

(56) References Cited

U.S. PATENT DOCUMENTS

| 7,884,949 B2 * | 2/2011 | Koh ................... G01B 11/2518 356/237.1 |
| 2008/0309881 A1 | 12/2008 | Huang et al. |

(Continued)

FOREIGN PATENT DOCUMENTS

| JP | 2010-529896 A | 9/2010 |
| JP | 2012-161426 A | 8/2012 |

(Continued)

OTHER PUBLICATIONS

International Search Report dated Jun. 8, 2017, in connection with International Patent Application No. PCT/JP2016/080170, 5 pgs.

*Primary Examiner* — Mohammed A Hasan
(74) *Attorney, Agent, or Firm* — Chiesa Shahinian & Giantomasi PC

(57) ABSTRACT

An ophthalmic imaging apparatus according to an exemplary embodiment includes a three dimensional data generator, an analyzer, and a display controller. The three dimensional data generator generates three dimensional data by scanning a three dimensional region of a subject's eye using optical coherence tomography (OCT). The analyzer generates a plurality of analysis maps by analyzing a plurality of pieces of partial three dimensional data in the three dimensional data. The display controller displays the plurality of analysis maps over a front image of the subject's eye on a display device.

9 Claims, 10 Drawing Sheets

(51) Int. Cl.
*A61B 3/12* (2006.01)
*G06T 7/00* (2017.01)

(52) U.S. Cl.
CPC .............. *A61B 3/12* (2013.01); *G06T 7/0016* (2013.01); *G06T 2207/10076* (2013.01); *G06T 2207/10101* (2013.01); *G06T 2207/30041* (2013.01)

(58) Field of Classification Search
USPC ........................................................ 351/206
See application file for complete search history.

(56) References Cited

U.S. PATENT DOCUMENTS

| | | | |
|---|---|---|---|
| 2011/0170062 A1 | 7/2011 | Isogai et al. | |
| 2012/0127428 A1* | 5/2012 | Isogai ..................... | A61B 3/102 351/206 |
| 2014/0112562 A1* | 4/2014 | Yamakawa ............ | A61B 3/102 382/131 |
| 2014/0316758 A1* | 10/2014 | Yagi ....................... | A61B 34/25 703/9 |
| 2015/0116664 A1 | 4/2015 | Uchida | |
| 2016/0302664 A1 | 10/2016 | Yamakawa et al. | |

FOREIGN PATENT DOCUMENTS

| | | |
|---|---|---|
| JP | 2015-080677 A | 4/2015 |
| JP | 2015-084865 A | 5/2015 |

\* cited by examiner

OPHTHALMIC IMAGING APPARATUS AND OPHTHALMIC INFORMATION PROCESSING APPARATUS

CROSS-REFERENCE TO RELATED APPLICATIONS

This application is a national stage (under 35 U.S.C. 371) of International Patent Application No. PCT/JP2016/080170, filed Oct. 12, 2016, claiming priority to Japanese Patent Application No. 2015-205049, filed Oct. 16, 2015, both of which are herein incorporated by reference in their entirety.

FIELD

Embodiments described herein relate generally to an ophthalmic imaging apparatus and an ophthalmic information processing apparatus.

BACKGROUND

An optical coherence tomography apparatus is known as an ophthalmic imaging apparatus for imaging a subject's eye. The optical coherence tomography apparatus can acquire cross-sectional images and three dimensional images of the eye fundus, the anterior eye segment, etc. by using optical coherence tomography (OCT). Further, the data acquired by the optical coherence tomography apparatus is utilized for an analysis process for grasping the state or condition of the subject's eye (see, for example, Patent Document 1 below).

Examples of the analysis process include the analysis of the thickness of a layer tissue of an eye fundus (fundus layer thickness analysis, for short). In the fundus layer thickness analysis, the generation of the thickness distribution of a predetermined layer tissue, the comparison with a normal eye database, or the like is carried out. The layer tissue to be analyzed is, for example, the retinal nerve fiber layer (RNFL), the ganglion cell layer (GCL), the composite layer (GCL+) of the ganglion cell layer and the inner plexiform layer (IPL), the composite layer (GCL++) of the ganglion cell layer, the inner plexiform layer, and the retinal nerve fiber layer, or the like.

[Patent Document 1] Japanese Unexamined Patent Application Publication No. 2012-161426

In some cases, it may be desirable to perform the analysis process over a wide region. For example, in the fundus layer thickness analysis relating to glaucoma, it is desirable to cover both a peripheral region of the optic nerve head and a region including the fovea centralis. In the conventional technique, the data collection for the peripheral region of the optic nerve head and the data collection for the region including the fovea centralis are performed separately from each other, and the two pieces of collected data are individually analyzed. Furthermore, in many conventional techniques, the result of the analysis for the peripheral region of the optic nerve head and the result of the analysis for the region including the fovea centralis are presented as separate pieces of data. Therefore, it is difficult to grasp the state of the fundus over the wide region with ease.

There is also a technique for synthesizing and displaying the result of the analysis for the peripheral region of the optic nerve head and the result of the analysis for the region including the fovea centralis. However, since the two analysis results are based on the two pieces of data collected separately from one another, an error may be present between the analysis results and an error may occur in the registration of the analysis results. As the result of such errors, the accuracy of the result of the analysis may deteriorate.

SUMMARY OF THE EMBODIMENTS

An object of the ophthalmic imaging apparatus and the ophthalmic information processing apparatus according to the embodiments is to present a highly accurate analysis result over a wide region of the subject's eye in a manner that can be grasped with ease.

An ophthalmic imaging apparatus according to an exemplary embodiment includes a three dimensional data generator, an analyzer, and a display controller. The three dimensional data generator generates three dimensional data by scanning a three dimensional region of a subject's eye using optical coherence tomography (OCT). The analyzer generates a plurality of analysis maps by analyzing a plurality of pieces of partial three dimensional data in the three dimensional data. The display controller displays the plurality of analysis maps over a front image of the subject's eye on a display device.

An ophthalmic information processing apparatus according to an exemplary embodiment includes a three dimensional data receiver, an analyzer, and a display controller. The three dimensional data receiver receives three dimensional data generated by scanning a three dimensional region of a subject's eye using optical coherence tomography (OCT). The analyzer generates a plurality of analysis maps by analyzing a plurality of pieces of partial three dimensional data in the three dimensional data. The display controller displays the plurality of analysis maps over a front image of the subject's eye on a display device.

According to the embodiment, it becomes possible to present a highly accurate analysis result over a wide region of the subject's eye in a manner that can be grasped with ease.

DETAILED DESCRIPTION OF THE EMBODIMENTS

Figure 1:
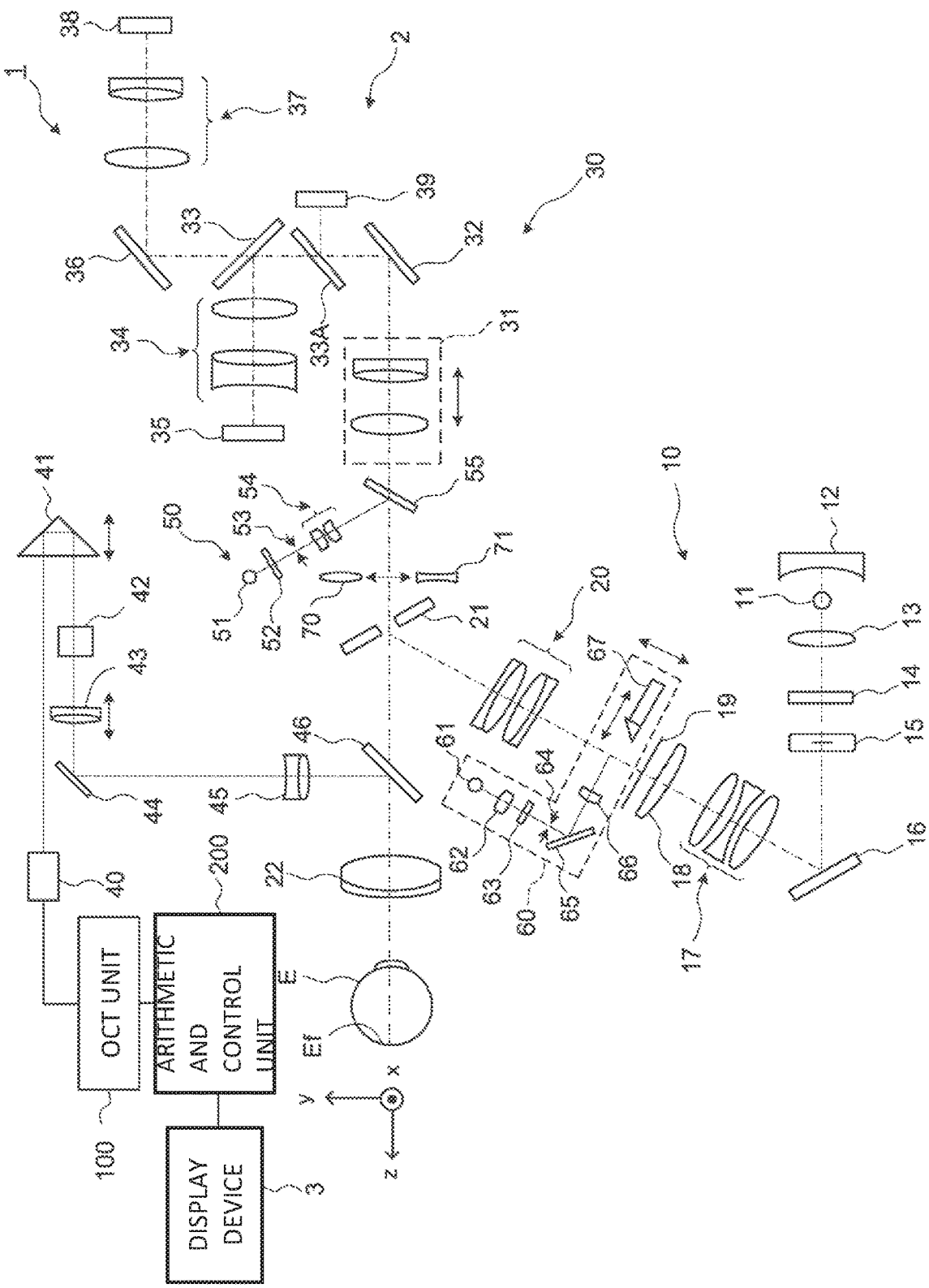
FIG. 1 is a schematic diagram illustrating an example of the configuration of the ophthalmic imaging apparatus according to the present embodiment.

Embodiments of the present invention will be described in detail with referring to the drawings. The ophthalmic imaging apparatus according to the embodiment functions at least as an optical coherence tomography apparatus and may further have the function of acquiring a front image of the subject's eye. As the function of acquiring front images, a fundus camera (also called a retinal camera) or a scanning laser ophthalmoscope (SLO) may be employed. Further, the function of generating a front image based on three dimensional data acquired by the optical coherence tomography apparatus may be employed. These functions will be described later.

In the case where the ophthalmic imaging apparatus does not have the function of acquiring a front image, the ophthalmic imaging apparatus may have the function for inputting a front image of the subject's eye acquired by another apparatus (e.g., a fundus camera, an SLO, or an optical coherence tomography apparatus). When three dimensional data acquired by another optical coherence tomography apparatus is input, the ophthalmic imaging apparatus may have the function of constructing a front image from the input three dimensional data. The same applies to the ophthalmic information processing apparatus according to embodiments and the ophthalmic imaging apparatus (e.g., a fundus camera or an SLO) not having the OCT function. The front image and the three dimensional data are input through, for example, a network such as a LAN or via a recording medium.

The following embodiments apply OCT to the eye fundus; but OCT may be applied to a site of the eye other than the fundus. For example, an embodiment in which OCT is applied to the anterior eye segment can be employed.

The following embodiments describe the ophthalmic imaging apparatus capable of executing the Fourier domain OCT technique. In particular, the ophthalmic imaging apparatus according to the following embodiment is capable of executing the swept source OCT technique. Note that it is also possible to employ any type of OCT technique other than the swept source, such as the spectral domain OCT technique or the full field OCT technique (also called the enface OCT technique). In addition, the following embodiments describe the multifunctional apparatus that is a combination of a fundus camera and an optical coherence tomography apparatus; however, embodiments are not limited thereto as described above.

The contents of the document cited in the present specification can be incorporated as contents of the following embodiments.

<Configuration>

As shown in FIG. 1, the ophthalmic imaging apparatus 1 includes the fundus camera unit 2, the OCT unit 100, and the arithmetic and control unit 200. The fundus camera unit 2 has almost the same optical system as the conventional fundus camera. The OCT unit 100 includes an optical system and a mechanism for executing OCT. The arithmetic and control unit 200 includes a processor. A jaw holder and a forehead rest for supporting the face of the subject is provided at positions facing the fundus camera unit 2.

In the present specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The processor realizes the functions according to the embodiment, for example, by reading out and executing a program stored in a storage circuit or a storage device.

<Fundus Camera Unit 2>

The fundus camera unit 2 is provided with an optical system for photographing the fundus Ef of the subject's eye E. Examples of images obtained by photographing the fundus Ef (called fundus images, fundus photographs, or the like) include observation images and photographed images. An observation image is obtained, for example, by capturing a moving image using near-infrared light. A photographed image is, for example, a color image or a monochrome image obtained by using visible flash light, or is a monochrome image obtained using near-infrared flash light. In addition, the fundus camera unit 2 may be capable of acquiring fluorescence images such as fluorescein angiograms, indocyanine green angiograms, or autofluorescence images.

The fundus camera unit 2 includes the illumination optical system 10 and the photographing optical system 30. The illumination optical system 10 projects illumination light onto the subject's eye E. The photographing optical system 30 detects the returning light of the illumination light from the subject's eye E. The measurement light from the OCT unit 100 is directed to the subject's eye E through the optical path in the fundus camera unit 2, and the returning light thereof is directed to the OCT unit 100 through the same optical path.

The observation light source 11 of the illumination optical system 10 is, for example, a halogen lamp or a light emitting diode (LED). The light output from the observation light source 11 (called observation illumination light) is reflected by the reflection mirror 12 having a concave reflective surface, passes through the condenser lens 13, and becomes near-infrared light after passing through the visible cut filter 14. Further, the observation illumination light is once converged near the photographing light source 15, reflected by the mirror 16, and passes through the relay lenses 17 and 18, the diaphragm 19, and the relay lens 20. Then, the observation illumination light is reflected on the peripheral part (i.e., the surrounding area of the aperture part) of the aperture mirror 21, penetrates the dichroic mirror 46, and refracted by the objective lens 22, thereby illuminating the subject's eye E (in particular, the fundus Ef).

The returning light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the returning light passes through the half mirror 33A, is reflected by the dichroic mirror 33, and forms an image on the light receiving surface of the CCD image sensor 35 by the condenser lens 34. The CCD image sensor 35 detects the returning light at a predetermined frame rate, for example. Note that an observation image of the fundus Ef is acquired when the focus of the photographing optical system 30 is adjusted to the fundus Ef, and an observation image of the anterior eye segment is acquired when the focus is adjusted to the anterior eye segment.

The photographing light source 15 is, for example, a visible light source including a xenon lamp or an LED. The light output from the photographing light source 15 (called photographing illumination light) passes through the same route as that of the observation illumination light and is projected onto the fundus Ef. The returning light of the photographing illumination light from the subject's eye E passes through the same route as that of the returning light of the observation illumination light, is guided to the dichroic mirror 33, passes through the dichroic mirror 33, is reflected by the mirror 36, and forms an image on the light receiving surface of the CCD image sensor 38 by the condenser lens 37.

The liquid crystal display (LCD) 39 displays a fixation target for fixating the subject's eye E and a visual target used for visual acuity measurement. Part of the light output from the LCD 39 is reflected by the half mirror 33A, reflected by the mirror 32, travels through the photography focusing lens 31 and the dichroic mirror 55, and passes through the aperture part of the aperture mirror 21. The light having passed through the aperture part of the aperture mirror 21 penetrates the dichroic mirror 46, and is refracted by the objective lens 22, thereby being projected onto the fundus Ef. By changing the display position of the fixation target on the screen of the LCD 39, the fixation position of the subject's eye E can be changed.

The fundus camera unit 2 is provided with the alignment optical system 50 and the focus optical system 60. The alignment optical system 50 generates an alignment indicator used for the alignment of the optical system with respect to the subject's eye E. The focus optical system 60 generates a split indicator used for the focus adjustment with respect to subject's eye E.

The alignment light output from the LED 51 of the alignment optical system 50 travels through the diaphragms 52 and 53 and the relay lens 54, is reflected by the dichroic mirror 55, and passes through the aperture part of the aperture mirror 21. The light having passed through the aperture part of the aperture mirror 21 penetrates the dichroic mirror 46 and is projected onto the subject's eye E by the objective lens 22.

The cornea reflection light of the alignment light travels through the objective lens 22, the dichroic mirror 46 and the aperture part of the aperture mirror 21. Part of the cornea reflection light of the alignment light penetrates the dichroic mirror 55, passes through the photography focusing lens 31, is reflected by the mirror 32, passes through the half mirror 33A, is reflected by the dichroic mirror 33, and is projected onto the light receiving surface of the CCD image sensor 35 by the condenser lens 34. Based on the received image (called the alignment indicator image) by the CCD image sensor 35, manual alignment and/or automatic alignment can be performed as in the conventional manner.

The focus optical system 60 is moved along the optical path of the illumination optical system 10 (called the illumination optical path) in conjunction with the movement of the photography focusing lens 31 along the optical path of the photographing optical system 30 (called the photographing optical path). The reflection rod 67 can be inserted into and removed from the illumination optical path.

Before performing focus adjustment, the reflective surface of the reflection rod 67 is arranged in the slanted state in the illumination optical path. The focus light output from the LED 61 passes through the relay lens 62, is split into two light beams by the split indicator plate 63, passes through the two-hole diaphragm 64. The focus light, then, is reflected by the mirror 65, is converged on the reflective surface of the reflection rod 67 by the condenser lens 66, and is reflected by the reflective surface. Further, the focus light travels through the relay lens 20, is reflected by the aperture mirror 21, penetrates the dichroic mirror 46, and is refracted by the objective lens 22, thereby being projected onto the fundus Ef.

The fundus reflection light of the focus light passes through the same route as the cornea reflection light of the alignment light and is detected by the CCD image sensor 35. Based on the image (called the split indicator image) received by the CCD image sensor 35, manual alignment and/or automatic alignment can be performed as in the conventional manner.

The photographing optical system 30 includes the diopter correction lenses 70 and 71. The diopter correction lenses 70 and 71 can be selectively inserted into the photographing optical path between the aperture mirror 21 and the dichroic mirror 55. The diopter correction lens 70 is a positive (+) lens for correcting high hyperopia. The diopter correction lens 70 is a convex lens of +20D (diopter), for example. The diopter correction lens 71 is a negative (−) lens for correcting high myopia. The diopter correction lens 71 is a concave lens of −20D, for example. The diopter correction lenses 70 and 71 are attached to a turret plate, for example. The turret plate has a hole for the case where neither of the diopter correction lenses 70 and 71 is applied.

The dichroic mirror 46 couples the optical path for fundus photography and the optical path for OCT. The dichroic mirror 46 reflects the light of wavelength bands used for OCT and transmits the light for fundus photography. Listed from the OCT unit 100 side, the collimator lens unit 40, the optical path length (OPL) changing device 41, the optical scanner 42, the OCT focusing lens 43, the mirror 44, and the relay lens 45 are placed in the optical path for OCT.

The optical path length changing device 41 is movable in the directions indicated by the arrow in FIG. 1 to change the length of the OCT optical path. The change in the OCT optical path length can be utilized for correcting the optical path length according to the axial length of the subject's eye E, for adjusting the interference condition, and the like. The optical path length changing device 41 includes, for example, a corner cube and a mechanism for moving the corner cube.

The optical scanner 42 is placed at a position optically conjugate with the pupil of the subject's eye E. The optical scanner 42 changes the traveling direction of the measurement light LS that travels along the OCT optical path. With this, the subject's eye E is scanned with the measurement light LS. The optical scanner 42 is capable of deflecting the measurement light LS in an arbitrary direction on the xy plane. The optical scanner 42 includes, for example, a galvano mirror that deflects the measurement light LS in the x direction and a galvanometer mirror that deflects the measurement light LS in the y direction.

<OCT Unit 100>

Figure 2:
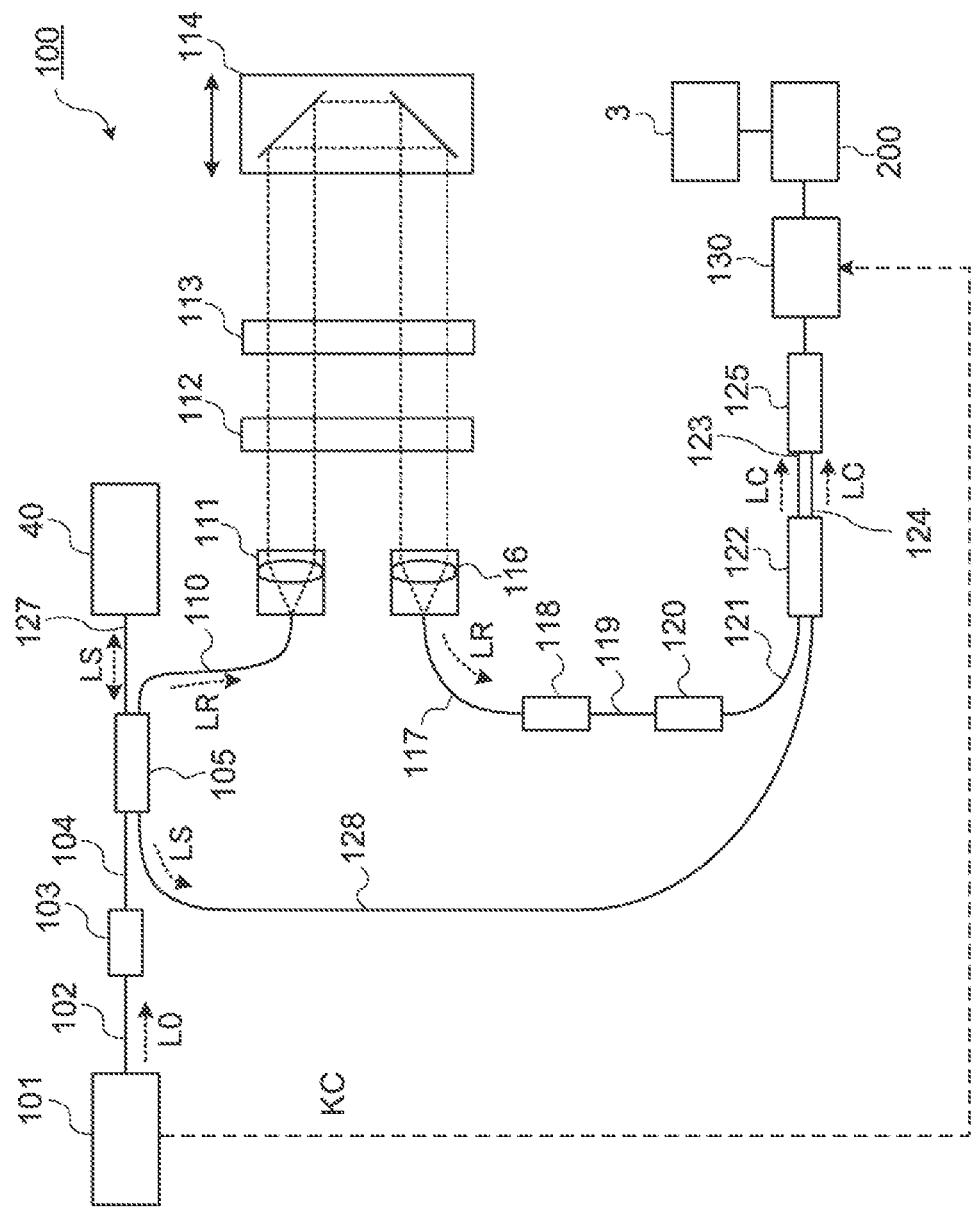
FIG. 2 is a schematic diagram illustrating an example of the configuration of the ophthalmic imaging apparatus according to the present embodiment.

As illustrated in FIG. 2, the OCT unit 100 is provided with the optical system for applying OCT to the subject's eye E. The configuration of the optical system is the same as that of the conventional swept source type optical coherence tomography apparatus. More specifically, the optical system includes the interference optical system configured to: split the light emitted from the light source of wavelength tunable type (also called wavelength scanning type) into measurement light and reference light; superpose the returning light of the measurement light from the subject's eye E and the reference light having traveled through the reference optical path to generate interference light; and detect the interference light. The detection result (i.e., detection signal) obtained by the interference optical system is a signal indicating the spectrum of the interference light. The detection signal is sent to the arithmetic and control unit 200.

The light source unit 101 includes a light source of wavelength tunable type (i.e., wavelength scanning type) that is capable of sweeping (or scanning) the wavelength of emitted light in the same manner as in ordinary optical coherence tomography apparatus of swept source type. The wavelength tunable type light source is, for example, a laser light source including a resonator. The light source unit 101 temporally changes the output wavelength in the near-infrared wavelength band, for example.

The light L0 output emitted from the light source unit 101 is guided to the polarization controller 103 through the optical fiber 102, and the polarization state of the light L0 is adjusted. Further, the light L0 is guided to the fiber coupler 105 through the optical fiber 104 and is split into the measurement light LS and the reference light LR.

The reference light LR is guided through the optical fiber 110 to the collimator 111, is converted into a parallel light beam, travels through the optical path length correction member 112 and the dispersion compensation member 113 and is guided to the corner cube 114. The optical path length correction member 112 acts to match the optical path length of the reference light LR and the optical path length of the measurement light LS. The dispersion compensation member 113 acts to match the dispersion characteristics between the reference light LR and the measurement light LS.

The corner cube 114 changes the traveling direction of the incident reference light LR in the opposite direction. The incident direction and the emitting direction of the reference light LR with respect to the corner cube 114 are parallel to each other. The corner cube 114 is movable along the incident direction of the reference light LR. With this, the optical path length of the reference light LR is changed.

In the configuration shown in FIGS. 1 and 2, the optical path length changing device 41 for changing the length of the optical path of the measurement light LS (called the measurement optical path or the measurement arm) and the corner cube 114 for changing the length of the optical path of the reference light LR (called the reference optical path or the reference arm) are provided. However, only one of the optical path length changing device 41 and the corner cube 114 may be provided. An optical member other these may be employed to change the difference between the measurement optical path length and the reference optical path length by using.

The reference light LR that has passed through the corner cube 114 travels through the dispersion compensation member 113 and the optical path length correction member 112, is converted from the parallel light beam to the convergent light beam by the collimator 116, and is incident on the optical fiber 117. The reference light LR incident on the optical fiber 117 is guided to the polarization controller 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided through the optical fiber 127 and is converted to a parallel light beam by the collimator lens unit 40. Then, the measurement light LS passes through the optical path length changing device 41, the optical scanner 42, the OCT focusing lens 43, the mirror 44, and the relay lens 45, and then reaches the dichroic mirror 46. The measurement light LS is reflected by the dichroic mirror 46, is refracted by the objective lens 22, and is incident on the subject's eye E. The measurement light LS is reflected and scattered at various depth positions of the subject's eye E. The returning light of the measurement light LS from the subject's eye E travels along the same route as the outward way in the opposite direction, is directed to the fiber coupler 105, and then reaches the fiber coupler 122 via the optical fiber 128.

The fiber coupler 122 superposes (i.e., interferes) the measurement light LS incident through the optical fiber 128 and the reference light LR incident through the optical fiber 121 with each other, to generate interference light. The fiber coupler 122 splits the interference light at a predetermined splitting ratio (e.g., 1 to 1) to generate a pair of interference light LC. The pair of the interference light LC is guided to the detector 125 through the optical fibers 123 and 124, respectively.

The detector 125 is, for example, a balanced photo diode. The balanced photodiode includes a pair of photodetectors for respectively detecting the pair of the interference light LC. The balanced photodiode outputs the difference between the pair of detection results obtained by the pair of photodetectors. The detector 125 sends the detection result (i.e., detection signal) to the data acquisition system (DAQ) 130.

The clock KC is supplied from the light source unit 101 to the DAQ 130. The clock KC is generated in the light source unit 101 in synchronization with the output timings of the respective wavelengths swept within a predetermined wavelength range by the wavelength tunable type light source. For example, the light source unit 101 splits the light L0 of each output wavelength to generate two pieces of split light, optically delays one of the two pieces of split light, generate the combined light of the two pieces of split light, and generates the clock KC based on the result of the detection of the combined light. The DAQ 130 performs the sampling of the detection signal input from the detector 125 based on the clock KC. The DAQ 130 sends the result of the sampling of the detection signal from the detector 125 to the arithmetic and control unit 200.

<Arithmetic and Control Unit 200>

The arithmetic and control unit 200 controls each part of the fundus camera unit 2, the display device 3, and the OCT unit 100. In addition, the arithmetic and control unit 200 executes various kinds of arithmetic processing. For example, the arithmetic and control unit 200 applies signal processing, such as the Fourier transform, to the spectral distribution based on the detection result obtained by the detector 125 for each series of wavelength scanning (i.e., for each A line). With this, the reflection intensity profile is formed for each A line. In addition, the arithmetic and control unit 200 applies imaging processing to the reflection intensity profiles for the respective A lines to form image data. The arithmetic processing for this purpose is the same as that of the conventional swept source OCT technique.

The arithmetic and control unit 200 includes, for example, a processor, a random access memory (RAM), a read only memory (ROM), a hard disk drive, a communication interface, and the like. Various computer programs are stored in a storage device such as a hard disk drive. The arithmetic and control unit 200 may include an operation device, an input device, a display device, and the like.

<Control System>

Figure 3:
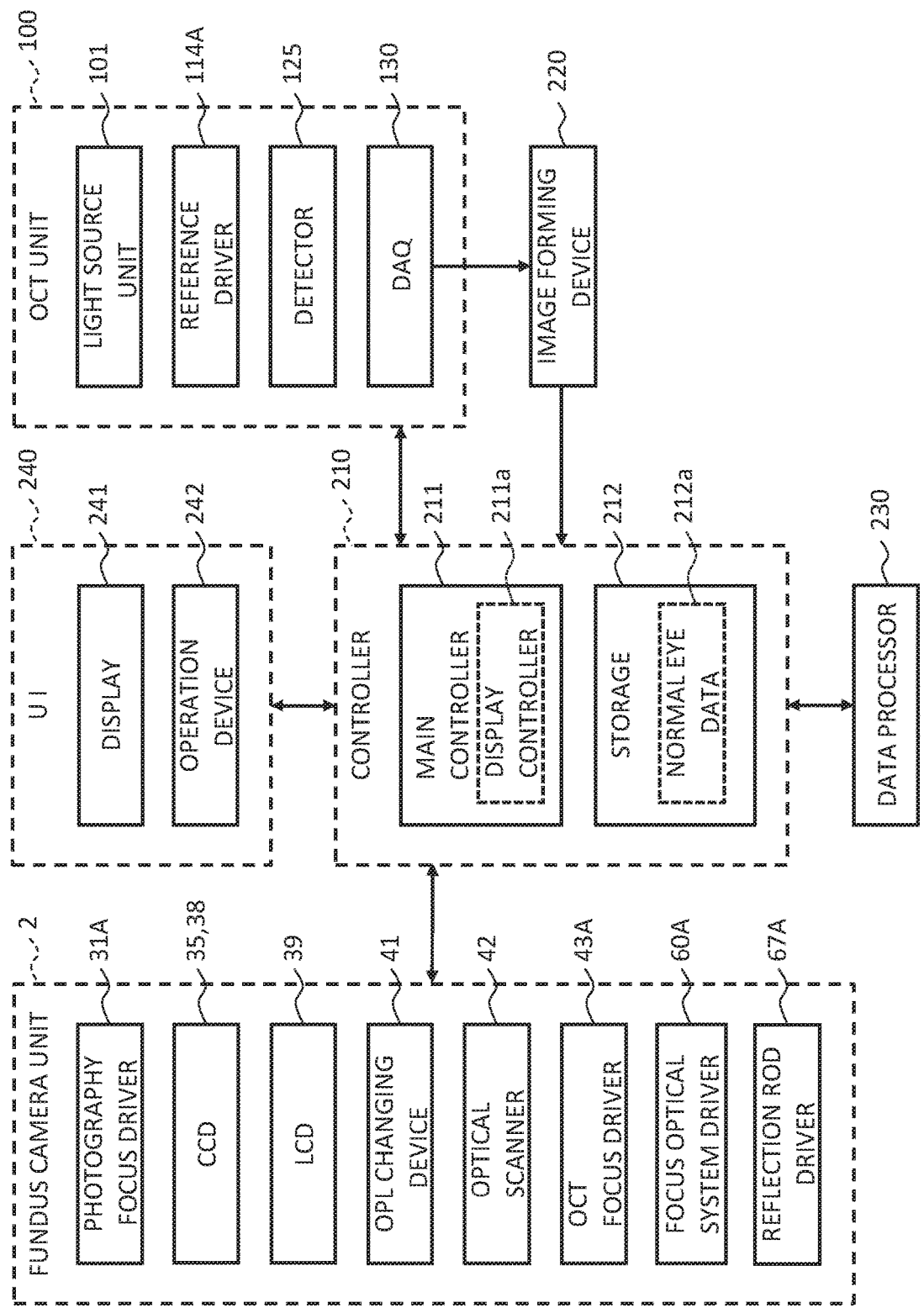
FIG. 3 is a schematic diagram illustrating an example of the configuration of the ophthalmic imaging apparatus according to the present embodiment.
Figure 4:
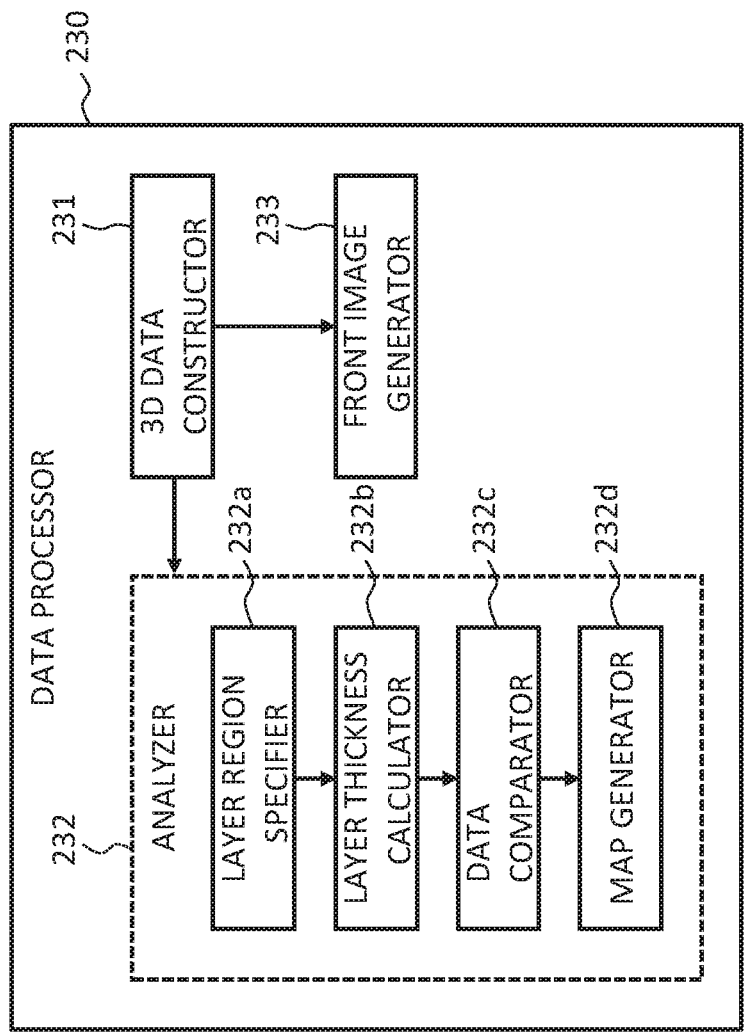
FIG. 4 is a schematic diagram illustrating an example of the configuration of the ophthalmic imaging apparatus according to the present embodiment.

An example of the configuration of the control system of the ophthalmic imaging apparatus 1 is shown in FIGS. 3 and 4.

<Controller 210>

The controller 210 controls each part of the ophthalmic imaging apparatus 1. The controller 210 includes a processor. The controller 210 is provided with the main controller 211 and the storage 212.

<Main Controller 211>

The main controller 211 performs various kinds of controls. For example, the main controller 211 controls the photography focus driver 31A, the CCDs (i.e., image sensors) 35 and 38, the LCD 39, the optical path length changing device 41, the optical scanner 42, the OCT focus driver 43A, the focus optical system driver 60A, the reflection rod driver 67A, etc. In addition, the main controller 211 controls the light source unit 101, the reference driver 114A, the detector 125, the DAQ 130, etc.

The photography focus driver 31A moves the photography focusing lens 31 along the optical axis of the photographing optical path. As the result, the focal position of the photographing optical system 30 changes. The OCT focus driver 43A moves the OCT focusing lens 43 along the optical axis of the measurement optical path. As the result, the focal position of the measurement light LS changes. The focal position of the measurement light LS corresponds to the depth position (i.e., z position) of the beam waist of the measurement light LS. The focus optical system driver 60A moves the focus optical system 60 along the optical axis of the illumination optical path. The main controller 211 controls the photography focus driver 31A and the focus optical system driver 60A in an interlocking manner. The reflection rod driver 67A inserts and removes the reflection rod 67 into and from the illumination optical path. The reference driver 114A moves the corner cube 114 provided in the reference optical path. As the result, the length of the reference optical path changes.

The ophthalmic imaging apparatus 1 may include an optical system driver that moves the fundus camera unit 2 (or the optical system included in it) in a three dimensional manner. For alignment and tracking, the main controller 211 controls the optical system driver. Note that tracking is the operation of moving the optical system to follow the movement of the subject's eye E after alignment and focus adjustment.

<Display Controller 211a>

The main controller 211 includes the display controller 211a. The display controller 211a executes various kinds of controls relating to information displayed on the display 241 and various kinds of controls for displaying information on the display 241. The processing executed by the display controller 211a will be described later.

<Storage 212>

The storage 212 stores various kinds of data. Examples of the data stored in the storage 212 include image data of OCT images, image data of fundus images, subject's eye information, and the like. The subject's eye information includes subject information such as the patient ID and the patient's name, identification information for the left eye/the right eye, electronic medical record information, and the like.

Further, the storage 212 stores the normal eye data 212a in advance in. The normal eye data 212a represents a normal range of a predetermined parameter regarding the structures, functions, characteristics, etc. of eyes. The parameter represents, for example, the thickness distribution of a predetermined layer tissue in retinas of normal eyes (called the normal layer thickness distribution). The normal layer thickness distribution includes layer thickness values at a plurality of positions within a predetermined area of eye fundus. The normal layer thickness distribution may be provided for two or more areas of eye fundus or may be provided for two or more layer tissues.

As a specific example, the normal eye data 212a includes a normal peripapillary RNFL thickness distribution and a normal macular GCL++ thickness distribution. The normal peripapillary RNFL thickness distribution represents the thickness distribution of the RNFL in a predetermined region around the optic nerve head. The normal macular GCL++ thickness distribution represents the thickness distribution of the GCL++ in a predetermined region including the fovea centralis.

Other examples of the normal eye data 212a include a parameter relating to the optic nerve head (e.g., the cup/disc ratio, the rim/disc ratio, the inclination state), a parameter relating to the lamina cribrosa (e.g., the thickness, the inclination state, the pore distribution), a parameter relating to the blood flow (e.g., the blood flow velocity, the blood flow amount), a parameter relating to the blood vessels (e.g., the blood vessel diameter), and a parameter relating to the anterior eye segment (e.g., the corneal thickness, the corner angle). The normal eye data 212a is not limited to those listed above.

The normal eye data 212a is constructed by statistically processing the values of a predetermined parameter obtained from OCT measurements of a plurality of normal eyes (i.e., healthy eyes) which have been diagnosed as having no disease. For example, the normal range of a parameter is determined by calculating the average value and the standard deviation of measurement values obtained from a plurality of normal eyes.

<Image Forming Device 220>

The image forming device 220 forms image data of a cross sectional image of the fundus Ef based on the sampling result of the detection signal input from the DAQ 130. This processing includes signal processing such as noise elimination (or noise reduction), filtering, fast Fourier transform (FFT for short), or the like as in the conventional swept source OCT technique. The image data formed by the image forming device 220 is a data set including a group of image data formed by applying imaging processing to the reflection intensity profiles for a plurality of A lines (i.e., lines along the z direction) arranged along a scan line. That is, the group of image data is a group of A scan image data.

In the present embodiment, the three dimensional scan is applied to the fundus Ef using OCT. Based on the data acquired through the three dimensional scan, the image forming device 220 forms a data set including a plurality of pieces of A scan image data arranged in the x direction and the y direction. The three dimensional scan means OCT scan applied to a three dimensional region of (the fundus Ef of) the subject's eye E. A typical example of the three dimensional scan is the raster scan. The raster scan is the scan along a plurality of parallel lines arranged in the xy plane. From the raster scan, data of the three dimensional region defined by the arrangement area of the scan lines in the xy plane and a predetermined area in the z direction is acquired. That is, from the raster scan, a data set including a plurality of pieces of A scan image data arranged in the x direction and the y direction is obtained. In other words, obtained is a data set including a plurality of pieces of A scan image data arranged at the positions determined by grid points (or lattice points).

In order to improve the image quality, it is possible to repeat the scan of the same pattern a plurality of times, and to synthesize (or average) the plurality of data sets obtained by the repetitive scan.

The image forming device 220 includes, for example, at least one of a processor and a dedicated circuit board. In the present specification, "image data" and an "image" based thereon may not be distinguished from each other. In addition, a site of the subject's eye E and an image representing the site may not be distinguished from each other.

<Data Processor 230>

The data processor 230 applies image processing and an analysis process to the image formed by the image forming device 220. For example, the data processor 230 applies correction processing such as the brightness correction or the dispersion correction to the images. In addition, the data processor 230 applies image processing or an analysis process to the image acquired by the fundus camera unit 2 (e.g., the eye fundus image, the anterior eye segment image). The data processor 230 includes, for example, at least one of a processor and a dedicated circuit board. The data processor 230 includes the three dimensional data constructor (3D data constructor for short) 231, the analyzer 232, and the front image generator 233.

<Three Dimensional Data Constructor 231>

As described above, when the three dimensional scan is applied to the fundus Ef, a three dimensional data set including a plurality of pieces of A scan image data arranged in the x direction and the y direction is obtained. The three dimensional data constructor 231 constructs three dimensional data of the fundus Ef based on the three dimensional data set. The three dimensional data may be the three dimensional data set itself or data obtained by processing the three dimensional data set.

Volume data is an example of the data obtained by processing the three dimensional data set. The volume data, also called voxel data, represents values on regular grids in a three dimensional space. The data processor 230 constructs volume data by executing known image processing. The known image processing includes the interpolation of pixels of the plurality of pieces of A scan image data included in the three dimensional data set, for example. When displaying an image on the basis of the volume data, the data processor 230 applies known rendering to the volume data.

<Analyzer 232>

The analyzer 232 analyzes a plurality of pieces of partial three dimensional data in the three dimensional data constructed by the three dimensional data constructor 231, to generate a plurality of analysis maps. The position (or area) of partial three dimensional data in the three dimensional data may be set in advance or may be set each time. In the former case, the analyzer 232, for example, specifies a set of pixels or voxels belonging to a predetermined area in the three dimensional data as partial three dimensional data. Further, the analysis map is information in which the result of analysis of the three dimensional data is represented as a distribution.

In the latter case, the analyzer 232, for example, analyzes the three dimensional data to specify the data region corresponding to a predetermined site of the fundus Ef, and sets partial three dimensional data with the specified data region as a reference. The process of specifying the data region includes, for example, the thresholding related to the level of the pixel values (e.g., brightness values), the shape recognition of the data region, or the like.

A specific example is described here. When the three dimensional scan is applied to a three dimensional region including the optic nerve head and the fovea centralis of the fundus Ef, the analyzer 232 specifies a papilla region corresponding to the optic nerve head in the three dimensional data. Then, the analyzer 232 sets a three dimensional data region of a predetermined size, wherein the three dimensional data region includes the papilla region specified, or the three dimensional data region is located around the papilla region specified. The three dimensional data region is called peripapillary three dimensional data. Here, the specification of the papilla region includes, for example, a process of specifying the image region corresponding to the retinal surface (i.e. the inner limiting membrane) and a process of searching for a deep and steep recess in the z direction in the image region specified. In addition, the analyzer 232 specifies a fovea centralis region corresponding to the fovea centralis in the three dimensional data. Then, the analyzer 232 sets a three dimensional data region of a predetermined size, wherein the three dimensional data region includes the fovea centralis region specified. The three dimensional data region is called macular three dimensional data. Here, the specification of the fovea centralis region includes, for example, a process of specifying the image region corresponding to the retinal surface and a process of searching for the center (or the deepest position) of a shallow and gentle recess in the z direction in the image region specified. Note that, in the above processes, the standard positions of the optic nerve head and the fovea centralis (or the macula) in eye fundus can be referred to, and the positional relationship between the optic nerve head and the fovea centralis (or the macula) can be referred to.

The sizes of the plurality of pieces of partial three dimensional data may be the same or different. For example, the macular three dimensional data is set to be larger than the peripapillary three dimensional data. Part of one partial three dimensional data may overlap with part of another partial three dimensional data. For example, it is possible to set the peripapillary three dimensional data and the macular three dimensional data in such a way that they partially overlap each other.

The analyzer 232 includes the layer region specifier 232a, the layer thickness calculator 232b, the data comparator 232c, and the map generator 232d.

<Layer Region Specifier 232a>

The layer region specifier 232a specifies the layer region corresponding to a predetermined layer tissue of the fundus Ef by analyzing the partial three dimensional data specified in the way as described above. The predetermined layer tissue is, for example, RNFL, GCL+, GCL++, or the like. The process of specifying a layer region is called segmentation. In general, the segmentation is performed based on brightness values of an OCT image (e.g., a two dimensional cross sectional image, a three dimensional image). respective layer tissues of the fundus Ef have distinctive reflectances, and hence the respective image regions corresponding to the layer tissues also have distinctive brightness values. In the segmentation, a target image region is specified based on such distinctive brightness values.

<Layer Thickness Calculator 232b>

The layer thickness calculator 232b calculates the thicknesses of the layer region specified by the layer region specifier 232a at a plurality of positions. The thickness of the layer region is measured, for example, as the distance between the upper surface (i.e., the surface on the fundus surface side) and the undersurface (i.e., the surface on the deep portion side of the fundus) of the layer region. This distance is measured, for example, along the z direction. For example, the plurality of positions at which the thicknesses to be measured is set to positions (e.g., x coordinate values and y coordinate values) corresponding to those of at least part of the plurality of pieces of A scan image data included in partial three dimensional data. With the layer thickness calculator 232*b* thus configured, a distribution of the thicknesses of a layer in the area of partial three dimensional data can be obtained.

<Data Comparator 232*c*>

The data comparator 232*c* compares the thicknesses of the layer region at the plurality of positions calculated by the layer thickness calculator 232*b* with the normal eye data 212*a* stored in the storage 212. The data comparator 232*c* performs scale adjustment and/or registration between the partial three dimensional data and the normal eye data 212*a* as necessary. In other words, the data comparator 232*c* is capable of associating the positions at which the thicknesses of the layer region are calculated, with the positions at which the normal eye data 212*a* (i.e., the normal layer thickness distribution) is defined.

In addition, the data comparator 232*c* compares the thickness value of the layer region with the normal layer thickness for each pair of associated positions. For example, the data comparator 232*c* determines whether or not the thickness value of the layer region is within the normal range for each pair of associated positions.

Further, the data comparator 232*c* can determine the degree of normality (or the degree of abnormality) of the thickness value of the layer region. For example, when the thickness value is included in the normal range, the data comparator 232*c* can determine the degree of normality based on the position of the thickness value in the normal range. In addition, when the thickness value is not included in the normal range, the data comparator 232*c* can determine the degree of abnormality based on the amount of deviation of the thickness value from the normal range.

<Map Generator 232*d*>

The map generator 232*d* generates an analysis map. There are various types of analysis maps. For example, the analysis map represents the thicknesses of the layer region obtained by the layer thickness calculator 232*b* using pseudo colors. In another example, the analysis map represents the result of the comparison between the thickness distribution of the layer region and the normal eye data 212*a* obtained by the data comparator 232*c* using pseudo colors.

The map generator 232*d* generates an analysis map corresponding to each of the plurality of pieces of partial three dimensional data set by the analyzer 232. With this, a plurality of analysis maps corresponding to the plurality of pieces of partial three dimensional data are obtained. At least some of the plurality of analysis maps may be of the same type or all of them may be different in type. Two or more analysis maps can be generated from a single partial three dimensional data. For example, it is possible to generate a layer thickness map and a layer thickness evaluation map from a single partial three dimensional data.

<Front Image Generator 233>

The front image generator 233 generates a front image based on three dimensional data of the fundus Ef acquired using OCT. Such a front image is called a OCT front image or an OCT enface image. Examples of the OCT front image include a C mode image (e.g., a xy cross sectional image, a horizontal cross sectional image), a projection image, a shadowgram, and the like. An image of an arbitrary cross section such as a C mode image is formed by selecting picture elements (e.g., pixels, voxels) on a designated cross section from three dimensional data. A projection image is formed by projecting three dimensional data in the z direction. A shadowgram is formed by projecting part of three dimensional data (for example, partial data corresponding to a specific layer) in the z direction. In addition, when a specific layer is selected by segmentation, it is possible to reconstruct the OCT front image so that the selected specific layer becomes flat. Such a front image is called a flattened image.

In this way, the front image generator 233 generates the OCT front image based on at least part of the three dimensional data. The three dimensional data used for generating the OCT front image may be the same as the three dimensional data analyzed by the analyzer 232, or may be three dimensional data acquired by applying OCT separately.

As will be described later, in the present embodiment, an analysis map is displayed over a front image. Here, the front image is an OCT front image or a front image of another type. The front image of another type may be a fundus photograph or a fundus scan image. The fundus photograph is a digital image obtained by photographing the fundus Ef using a fundus camera. The fundus camera may be the fundus camera unit 2 or another fundus camera. The fundus scan image is a digital image formed by scanning the fundus Ef using an SLO. It is also possible to use a front image acquired by a fundus imaging apparatus of a type other than a fundus camera and an SLO. In embodiments where an OCT front image is not utilized, the front image generator 233 need not be provided.

The data processor 230 can perform registration between a front image and three dimensional data of the fundus Ef. The registration includes, for example, a process of generating an OCT front image from the three dimensional data, a position matching process between the OCT front image and the front image of the fundus Ef, and a process of applying the result of the position matching to the three dimensional data.

<User Interface 240>

The user interface 240 includes the display 241 and the operation device 242. The display 241 includes the display device 3. The operation device 242 includes various kinds of operation devices and input devices. The user interface 240 may include a device, such as a touch panel, in which the display function and the operation function are integrated. It is also possible to construct an embodiment that does not include at least part of the user interface 240. For example, the display device may be an external device connected to the ophthalmic imaging apparatus.

<Operation>

Figure 5:
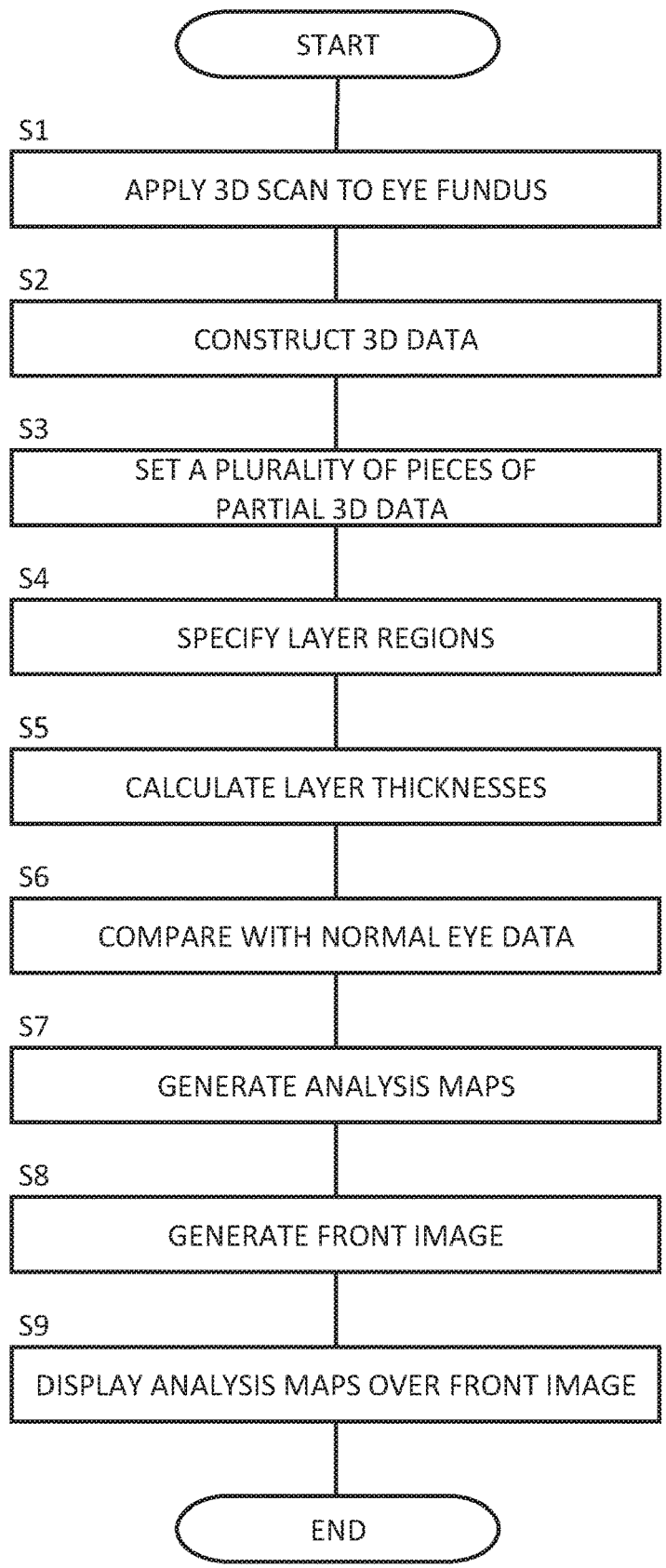
FIG. 5 is a flowchart illustrating an example of the operation of the ophthalmic imaging apparatus according to the present embodiment.

The operation of the ophthalmic imaging apparatus 1 will be described. An example of the operation is shown in FIG. 5.

(S1: Apply 3D Scan to Eye Fundus)

After performing preparatory operations such as alignment and focus adjustment, the ophthalmic imaging apparatus 1 applies three dimensional scan to the fundus Ef using OCT. In the present example, the scan is applied to a three dimensional region including the optic nerve head and the fovea centralis of the fundus Ef.

(S2: Construct Three Dimensional Data)

Based on the data acquired by the three dimensional scan in step S1, the image forming device 220 forms a plurality of pieces of A scan image data arranged in the x direction and the y direction. Based on the plurality of pieces of A scan image data, the three dimensional data constructor 231 constructs three dimensional data corresponding to the three dimensional region scanned in step S1.

Figure 6:
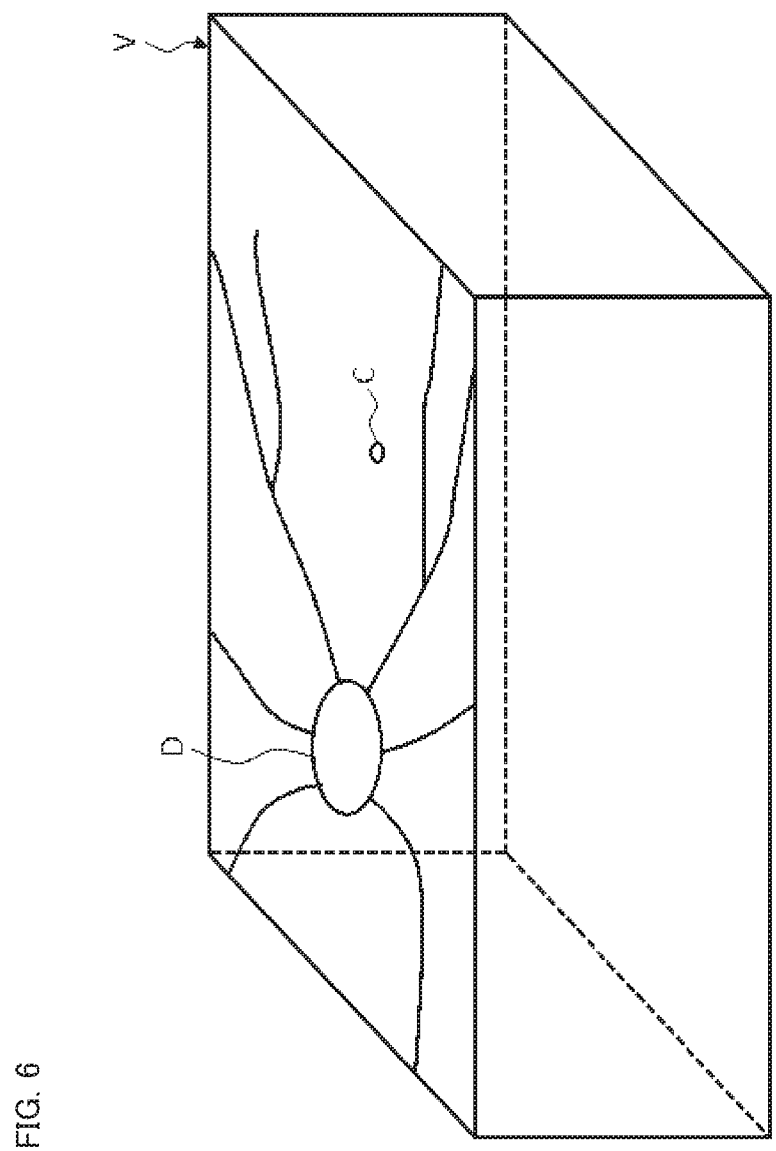
FIG. 6 is a schematic diagram for describing an example of the operation of the ophthalmic imaging apparatus according to the present embodiment.

FIG. 6 schematically shows the three dimensional data constructed in the present example. The three dimensional data V shown in FIG. 6 includes the papilla region D corresponding to the optic nerve head and the fovea centralis region C corresponding to the fovea centralis.

(S3: Set a Plurality of Pieces of Partial Three Dimensional Data)

Figure 7:
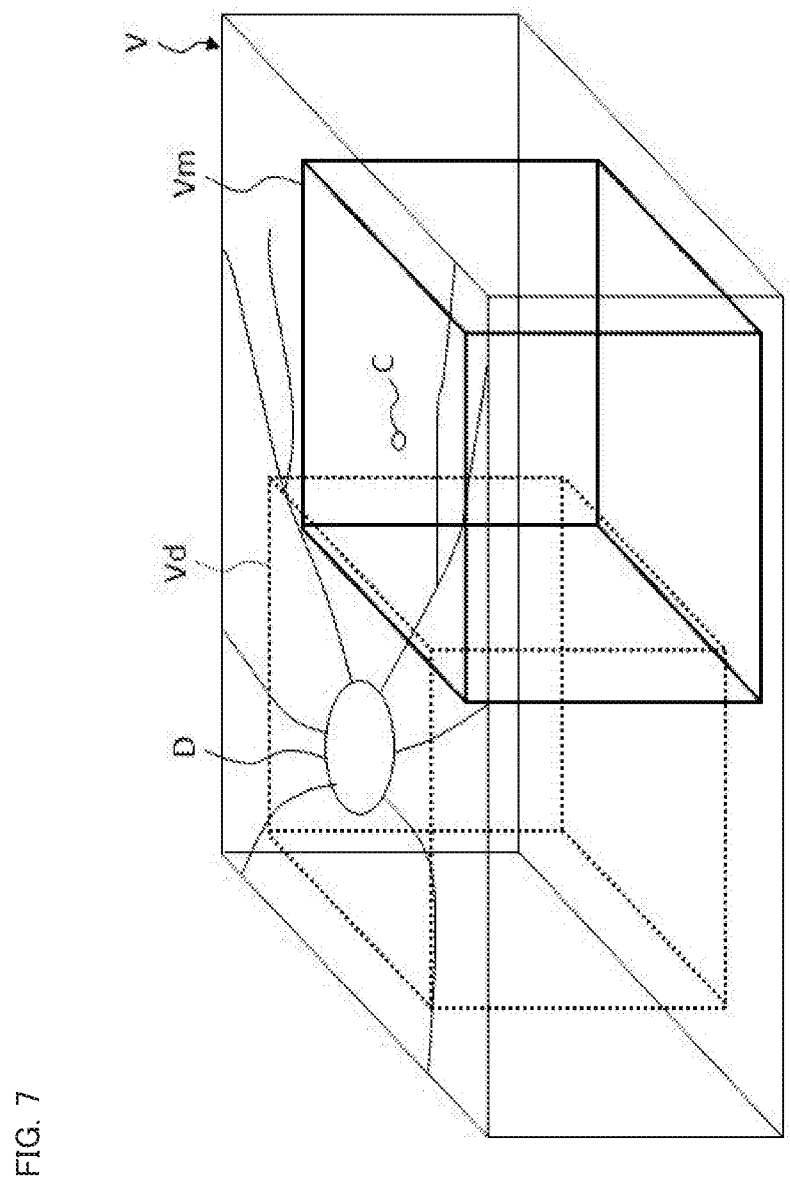
FIG. 7 is a schematic diagram for describing an example of the operation of the ophthalmic imaging apparatus according to the present embodiment.

The analyzer 232 sets a plurality of pieces of partial three dimensional data in the three dimensional data constructed in step S2. In the present example, as shown in FIG. 7, the peripapillary three dimensional data Vd including the papilla region D and the macular three dimensional data Vm including the fovea centralis region C are set. A part of the peripapillary three dimensional data Vd and a part of the macular three dimensional data Vm overlap each other.

(S4: Specify Layer Regions)

The layer region specifier 232a specifies a layer region corresponding to a predetermined layer tissue of the fundus Ef by analyzing each partial three dimensional data set in step S3. In the present example, the RNFL region in the peripapillary three dimensional data Vd is specified, and also the GCL++ region in the macular three dimensional data Vm is specified.

(S5: Calculate Layer Thicknesses)

The layer thickness calculator 232b calculates the thicknesses of each layer region specified in step S4 at a plurality of positions. In the present example, the RNFL thickness distribution in the peripapillary three dimensional data Vd and the GCL++ thickness distribution in the macular three dimensional data Vm are calculated.

(S6: Compare with Normal Eye Data)

The data comparator 232c compares the layer thickness distributions calculated in step S5 with the normal eye data 212a. In the present example, the RNFL thickness distribution in the peripapillary three dimensional data Vd obtained in step S5 is compared with the normal peripapillary RNFL thickness distribution included in the normal eye data 212a. In addition, the GCL++ thickness distribution in the macular three dimensional data Vm obtained in step S5 is compared with the normal macular GCL++ thickness distribution included in the normal eye data 212a.

(S7: Generate Analysis Maps)

The map generator 232d generates analysis maps on the basis of the comparison results obtained in step S6. In the present example, a peripapillary layer thickness evaluation map is generated in which the comparison results between the RNFL thickness distribution in the peripapillary three dimensional data Vd and the normal peripapillary RNFL thickness distribution are expressed using pseudo colors. In addition, a macular layer thickness evaluation map is generated in which the comparison results between the GCL++ thickness distribution in the macular three dimensional data Vm and the normal macular GCL++ thickness distribution are expressed using pseudo colors.

(S8: Generate Front Image)

The ophthalmic imaging apparatus 1 generates a front image of the fundus Ef by photographing the fundus Ef using the fundus camera unit 2 or by applying three dimensional scan to the fundus Ef using OCT. Alternatively, the ophthalmic imaging apparatus 1 acquires the front image of the fundus Ef obtained in the past from the outside.

(S9: Display Analysis Maps Over Front Image)

In the case where the front image is generated based on the three dimensional data acquired in step S2, that is, in the case where both the analysis maps and the front image are generated from the same three dimensional data, registration between the analysis maps and the front image need not be performed. When a front image different from this is used, for example, the data processor 230 performs registration between the three dimensional data acquired in step S2 and the front image, and carries out registration between the analysis maps and the front image using the result of the registration between the three dimensional data and the front image. The display controller 211a displays the analysis maps generated in step S7 on the front image generated in step S8.

<Display Mode>

Figure 8A:
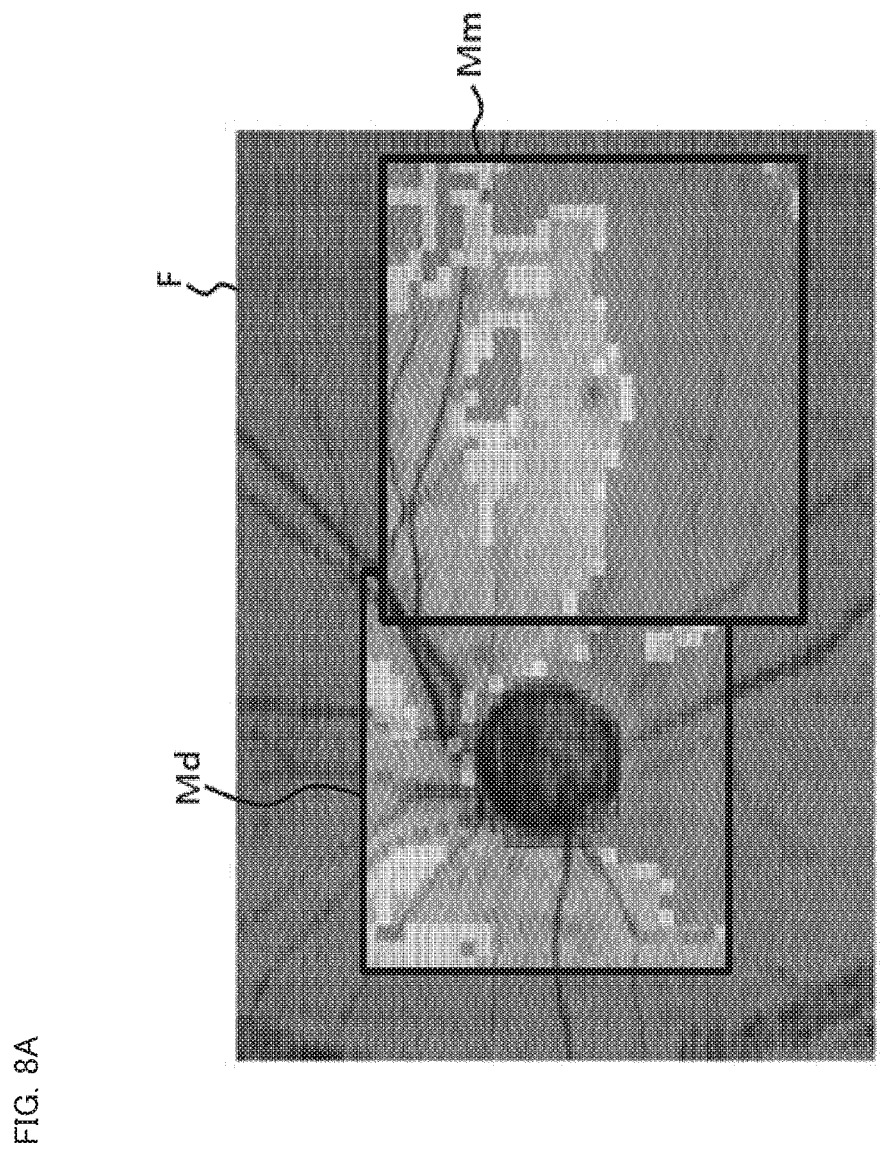
FIG. 8A is a schematic diagram for describing an example of the operation of the ophthalmic imaging apparatus according to the present embodiment.

The display mode of the front image and the analysis maps will be described. FIG. 8A illustrates an example of the display mode in the operation example described above. In the display example shown in FIG. 8A, the peripapillary layer thickness evaluation map Md and the macular layer thickness evaluation map Mm are displayed over the front image F. In the present example, the peripapillary three dimensional data Vd and the macular three dimensional data Vm partially overlaps each other. In the display example shown in FIG. 8A, the macular layer thickness evaluation map Mm is placed over the peripapillary layer thickness evaluation map Md in their overlapping regions. In contrast to this, the peripapillary layer thickness evaluation map Md may be placed over the macular layer thickness evaluation map Mm. In addition, it is also possible to display the peripapillary layer thickness evaluation map Md and the macular layer thickness evaluation map Mm on different layers, and to arbitrarily set the opacity (e.g., alpha value) of the upper layer so that both maps can be visually recognized.

Figure 8B:
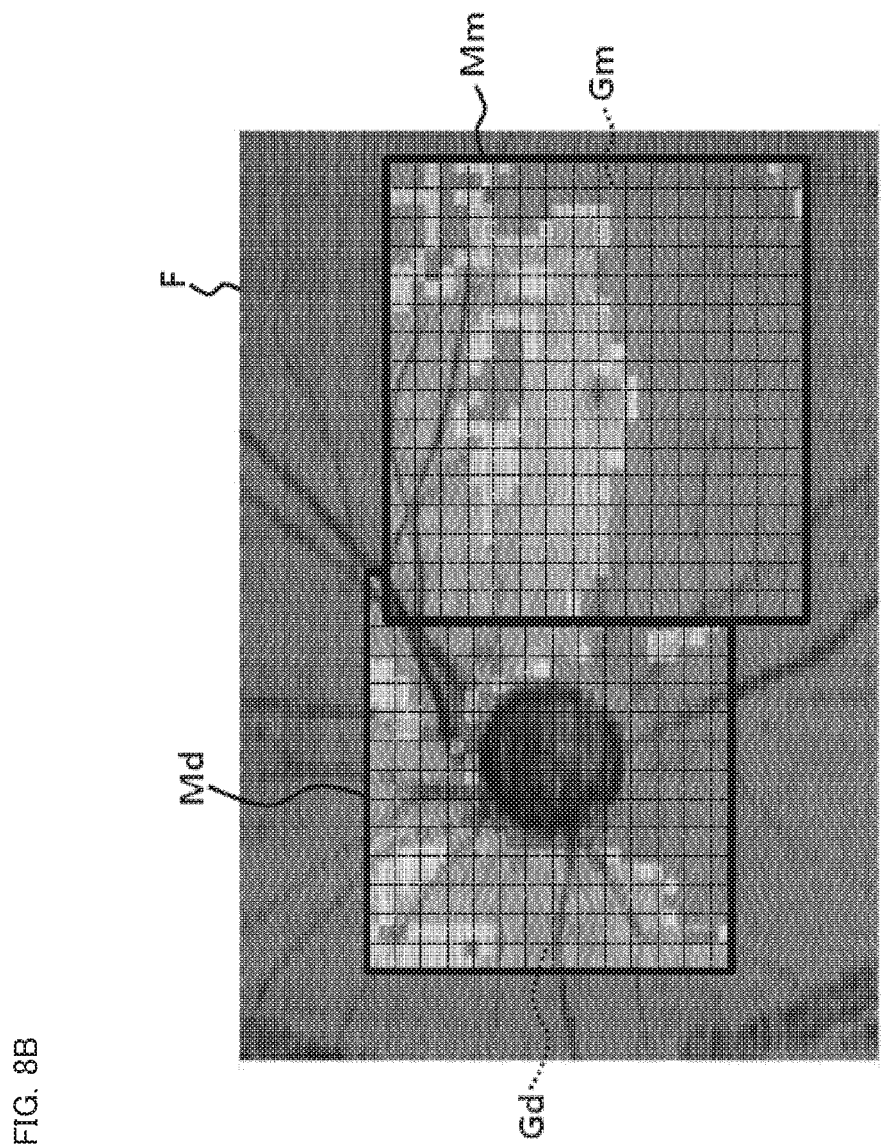
FIG. 8B is a schematic diagram for describing an example of the operation of the ophthalmic imaging apparatus according to the present embodiment.

Another example of the display mode is illustrated in FIG. 8B. In the display example shown in FIG. 8B, the grid images Gd and Gm are displayed in addition to the display example of FIG. 8A. The grid image Gd is displayed over the peripapillary layer thickness evaluation map Md, and the grid image Gm is displayed over the macular layer thickness evaluation map Mm. Each of the grid images Gd and Gm is generated based on the unit regions of the analysis process executed by the analyzer 232. As described above, the analysis process is applied to each of the plurality of A lines arranged in the x direction and the y direction, for example. In this case, the unit regions of the analysis process may be defined to be the sections of a grid (or a lattice) whose grid points correspond to the positions of the A lines, for example. Alternatively, the unit region may be defined by a grid in which the centers of the sections are arranged at the positions of the A lines. Each of the grid images Gd and Gm is generated by, for example, multiplying the grid section defined in this way by an integer N in the horizontal direction (i.e. the x direction) and the vertical direction (i.e. the y direction), respectively. Here, the integer N is equal to or larger than 1. It should be noted that a grid image(s) may be displayed only on one or more of analysis maps displayed together with a front image, or grid images may be displayed on all of the analysis maps.

As described above, in the case where two or more of the plurality of pieces of partial three dimensional data are partially overlapped one another, the display controller 211a can display two or more analysis maps based on the two or more pieces of partial three dimensional data partially overlapping one another. In such a case, the overlap order of the analysis maps (that is, the arrangement of the overlapped analysis maps) can be set according to a predetermined condition.

For example, it is possible to set the overlap order of the analysis maps according to sites of eye. More specifically, based on two or more sites of the subject's eye E corresponding to the two or more pieces of partial three dimensional data partially overlapping one another, the display controller 211a can determine the order of the two or more analysis maps generated from the two or more pieces of partial three dimensional data. Then, the display controller 211a can display the two or more analysis maps partially overlapping one another in accordance with the order determined. The information that associates sites of eye with orders (or, priorities or ranks) is stored in advance in the storage 212. The user may be edit the information as desired. In the above example, the rank of the macula is set higher than that of the optic nerve head, for example. By referring to the information, the display controller 211a arranges the macular layer thickness evaluation map Mm on the peripapillary layer thickness evaluation map Md, and displays these evaluation maps over the front image F.

As another example, the overlap order of the analysis maps can be set according to the types of analyses. Examples of the analysis types include the types of analysis software, the types of layer regions to be analyzed, and the like. The analyzer 232 at least executes a first analysis process on part of the two or more pieces of partial three dimensional data partially overlapping one another, and executes a second analysis process different from the first analysis process on another part thereof. Based on the types of analysis processes executed by the analyzer 232, the display controller 211a determines the order of the two or more analysis maps generated from the two or more pieces of partial three dimensional data, and displays the two or more analysis maps partially overlapping one another according to the order determined. The information that associates analysis types with orders ((or, priorities or ranks) is stored in advance in the storage 212. The user may be edit the information as desired. In the above example, the rank of the GCL++ thickness analysis is set higher than that of the RNFL thickness analysis, for example. By referring to the information, the display controller 211a arranges the macular layer thickness evaluation map Mm on the peripapillary layer thickness evaluation map Md, and displays these evaluation maps over the front image F.

<Actions and Effects>

The actions and effects of the ophthalmic imaging apparatus according to embodiments will be described.

An ophthalmic imaging apparatus according to embodiments includes a three dimensional data generator, an analyzer, and a display controller. The three dimensional data generator generates three dimensional data by scanning a three dimensional region of a subject's eye using OCT. The analyzer generates a plurality of analysis maps by analyzing a plurality of pieces of partial three dimensional data in the three dimensional data. The display controller displays the plurality of analysis maps over a front image of the subject's eye on a display device.

According to this configuration, a plurality of parts of the subject's eye can be analyzed based on a single three dimensional data, and maps representing the result of the analyses can be displayed together with the front image of the subject's eye.

In the exemplary embodiment described above, the three dimensional data generator includes the OCT unit 100, the measurement optical path in the fundus camera unit 2, the image forming device 220, and the three dimensional data constructor 231. The analyzer includes the analyzer 232. The display controller includes the display controller 211a. Further, the display device may be included in the ophthalmic imaging apparatus, or it may be an external device connected to the ophthalmic imaging apparatus.

In embodiments, the three dimensional data generator may be configured to scan a three dimensional region of the fundus of the subject's eye to generate the three dimensional data. In this case, the front image may be a fundus image acquired by a fundus camera, a fundus scan image acquired by a scanning laser ophthalmoscope, or an OCT front image generated from at least part of three dimensional data of the fundus acquired using OCT.

The OCT front image may be generated from the same three dimensional data as the three dimensional data for obtaining the plurality of analysis maps, or may be generated from another three dimensional data. Further, the front image is not limited to these. In addition, when analyzing other sites of the subject's eye, a front image of the relevant site is obtained. For example, when the anterior eye segment is analyzed, a frame of an observation image, a photographed image, an OCT front image, or the like can be used.

In the above exemplary embodiment, the fundus camera unit 2 can be used to acquire the fundus image, or the front image generator 233 can be used to generate the OCT front image. It is also possible to acquire an arbitrary front image such as a fundus image, a fundus scan image, or an OCT front image from an external device. The external device is, for example, an image archiving system such as PACS, an ophthalmic imaging apparatus, etc. Alternatively, an arbitrary front image may be read out from a recording medium.

In addition, the analyzer may include a layer region specifier and a layer thickness calculator. The layer region specifier specifies a layer region corresponding to a predetermined layer tissue of the fundus by analyzing at least one of the plurality of pieces of partial three dimensional data in the three dimensional data. Analysis other than the analysis of the layer of the fundus, such as optical nerve head shape analysis or drusen analysis, may be applied to at least one of the plurality of pieces of partial three dimensional data. Alternatively, the layer analysis may be applied to all of the plurality of pieces of partial three dimensional data. The layer thickness calculator calculates the thicknesses at a plurality of positions of the layer region specified by the layer region specifier. The analyzer is capable of generating an analysis map based on the thicknesses of the layer region calculated at the plurality of positions.

According to this configuration, the analysis map representing the thickness distribution of the predetermined layer tissue in an area of the partial three dimensional data can be obtained.

In the above exemplary embodiment, the layer region specifier includes the layer region specifier 232a, the layer thickness calculator includes the layer thickness calculator 232b, and the generation of the analysis map is performed by the map generator 232d.

Further, the ophthalmic imaging apparatus of embodiments may include a storage and the analyzer may include a comparator. In the storage, normal eye data is stored in advance. The normal eye data represents the distribution of allowable range of the thickness of the predetermined layer tissue for normal eyes. The comparator in the analyzer compares the thicknesses of the layer region at the plurality of positions calculated by the layer thickness calculator, with the normal eye data. The analyzer can generate a layer thickness evaluation map based on the comparison result obtained by the comparator. The layer thickness evaluation map generated is used as an analysis map and is displayed together with the front image.

According to this configuration, it is possible to acquire and visually present information indicating whether or not there is abnormality in the thickness of the predetermined layer tissue, information indicating the degree of abnormality, or the like.

In the above exemplary embodiment, the storage includes the storage 212, the normal eye data includes the normal eye data 212a, the comparator includes the data comparator 232c, and the generation of the layer thickness evaluation map is performed by the map generator 232d.

In addition, the three dimensional data generator may be configured to scan a three dimensional region including the optic nerve head and the fovea centralis of the fundus, to generate the three dimensional data. Further, the analyzer may be configured to at least analyze the first partial three dimensional data (e.g., the peripapillary three dimensional data) corresponding to a partial three dimensional region including the optic nerve head (e.g., the papilla region) to generate the first layer thickness evaluation map (e.g., the peripapillary layer thickness evaluation map), and to analyze the second partial three dimensional data (e.g., the macular three dimensional data) corresponding to a partial three dimensional region including the fovea centralis (e.g., the fovea centralis region) to generate the second layer thickness evaluation map (e.g., the macular layer thickness evaluation map). The display controller can display at least the first layer thickness evaluation map and the second layer thickness evaluation map over the front image.

According to this configuration, it becomes possible to comprehensively grasp the state of the layer thickness around the optic nerve head and the state of the layer thickness in the macula, which is effective for diagnosis of glaucoma etc.

In the case where the first partial three dimensional data (e.g., the peripapillary three dimensional data) and the second partial three dimensional data (e.g., the macular three dimensional data) partially overlap each other, the display controller can display part of the first layer thickness evaluation map (e.g., the peripapillary layer thickness evaluation map) and part of the second layer thickness evaluation map (e.g., the macular layer thickness evaluation map) overlapping each other. For example, the display controller can display the first layer thickness evaluation map (e.g., the peripapillary three dimensional data) and the second layer thickness evaluation map (e.g., the macular three dimensional data) in such a manner that a part of the second layer thickness evaluation map is displayed over the first layer thickness evaluation map.

More generally, in a case where two or more of the plurality of pieces of partial three dimensional data in the three dimensional data are partially overlapped one another, the display controller can display two or more analysis maps based on the two or more pieces of partial three dimensional data partially overlapping one another.

At this time, the display controller can determine the order of the two or more analysis maps based on two or more sites of the subject's eye corresponding to the two or more pieces of partial three dimensional data, and display the two or more analysis maps partially overlapping one another according to the order determined. In other words, the display controller can determine the order of overlapping the two or more analysis maps according to the sites to be analyzed.

Alternatively, when the analyzer at least executes the first analysis process on part of the two or more pieces of partial three dimensional data, and executes the second analysis process different from the first analysis process on another part thereof, that is, when the analyzer executes different types of analysis processes, it is possible to determine the order of overlapping the two or more analysis maps according to the types of analysis processes applied. In other words, the display controller may be configured to determine the order of the two or more analysis maps based on the types of analysis processes executed by the analyzer, and display the two or more analysis maps partially overlapping one another according to the order determined.

In embodiments, the display controller can display a grid image based on a unit region of an analysis process executed by the analyzer, over at least one of the plurality of analysis maps. In addition, it is possible to automatically determine the presence or absence of display of the grid image according to the types of the analysis maps. Further, it is also possible for the user to select whether or not to display the grid image.

According to the present embodiment configured as above, unlike the conventional technique of individually acquiring and analyzing data about a plurality of sites of the subject's eye, a plurality of analysis maps can be generated from a single three dimensional data acquired using OCT. Therefore, the risk of an error between the analysis maps and the risk of an error in registration are reduced, and therefore the analysis result can be obtained with high accuracy. Further, according to the present embodiment, a plurality of analysis maps can be displayed over a front image of subject's eyes. This makes it possible for the user to easily grasp the state of the subject's eye over a wide region. In this way, according to the present embodiment, it is possible to present the analysis result of high accuracy over a wide region of the subject's eye in a manner that can be easily grasped.

<Ophthalmic Information Processing Apparatus>

An ophthalmic information processing apparatus according to embodiments includes one or more information processing apparatuses and may further include a display device. Also, the ophthalmic information processing apparatus may have a function as an ophthalmic imaging apparatus such as a fundus camera or an SLO.

Figure 9:
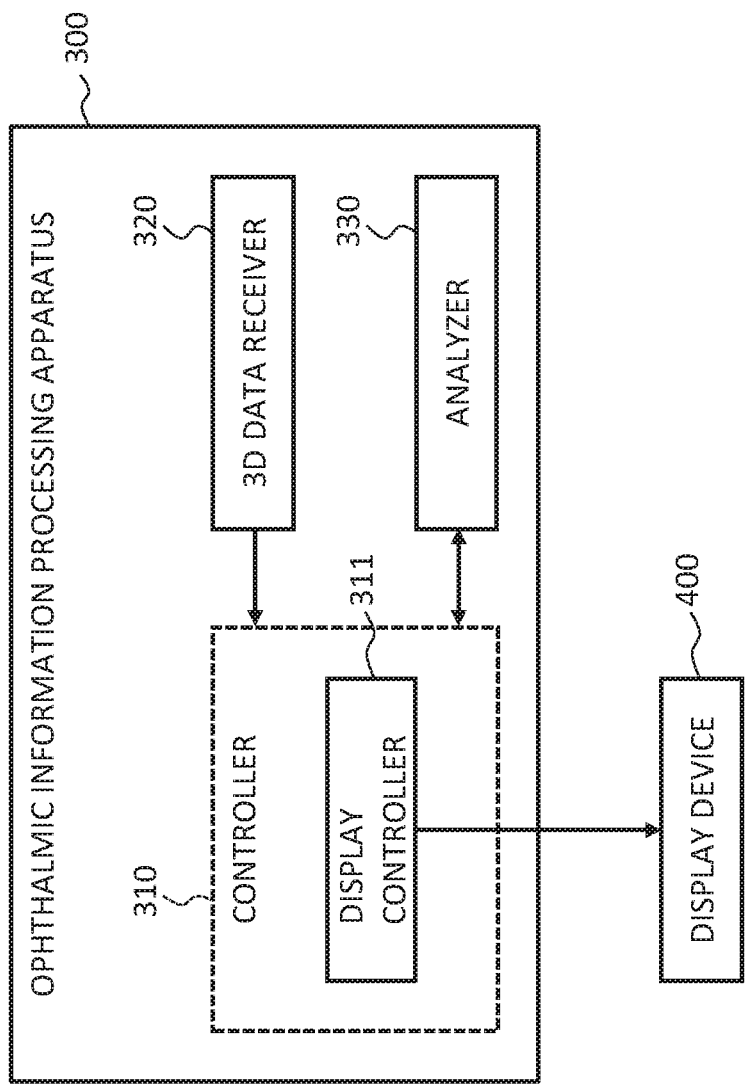
FIG. 9 is a schematic diagram illustrating an example of the configuration of the ophthalmic information processing apparatus according to the present embodiment.

FIG. 9 illustrates an example of the configuration of the ophthalmic information processing apparatus according to the present embodiment. The ophthalmic information processing apparatus 300 includes the controller 310, the three dimensional data receiver (3D data receiver for short) 320, and the analyzer 330.

The controller 310 controls each part of the ophthalmic information processing apparatus 300 (and an external device connected thereto). The controller 310 includes the display controller 311. The display controller 310 may have the same configuration as the display controller 211a of the ophthalmic imaging apparatus 1 described above, and may be capable of executing the same processing.

The three dimensional data receiver 320 receives three dimensional data generated by scanning a three dimensional region of the subject's eye using OCT. In the present embodiment, an ophthalmic imaging apparatus (i.e., an optical coherence tomography apparatus) different from the ophthalmic information processing apparatus 300 applies the three dimensional OCT scan to the subject's eye. The three dimensional data acquired by the ophthalmic imaging apparatus is directly or indirectly transmitted to the ophthalmic information processing apparatus 300. Examples of the direct transmission include: transmission via a LAN in a medical institution; transmission via the Internet; and transmission via a wide area dedicated line. Examples of the indirect transmission include: transmission via storage in an archiving system (e.g., an image archiving system, an electronic medical record system); transmission via an information processing computer terminal (e.g., a doctor's computer terminal, etc.); and transmission via recording in a recording medium (e.g., a semiconductor memory, an optical disk, a magneto-optical disk, a magnetic storage medium).

The three dimensional data receiver 320 has a configuration corresponding to the input mode of three dimensional data from the outside. For example, the three dimensional data receiver 320 includes a communication interface for communicating with an external device or a drive device for reading out data recorded in a recording medium. The communication interface conforms to a network to which the ophthalmic information processing apparatus 300 can connect. Examples of the communication interface include a network interface for a LAN, that for the Internet, and that for a wide area dedicated line.

In addition, the three dimensional data receiver 320 can receive a front image of the subject's eye. When the ophthalmic information processing apparatus 300 has a function as a fundus camera or an SLO, it is possible to use a front image acquired by the ophthalmic information processing apparatus 300 itself in the processing described later.

The three dimensional data receiver 320 sends the received three dimensional data (together with the subject ID, the front image, etc.) to the controller 310. The controller 310 sends the three dimensional data (and the subject ID, the front image, etc.) to the analyzer 330. For example, the analyzer 330 may have the same configuration as the analyzer 232 of the ophthalmic imaging apparatus 1 described above and may be capable of executing the same processing (see FIG. 4, etc.). The analyzer 330 generates a plurality of analysis maps by analyzing a plurality of pieces of partial three dimensional data in the three dimensional data input. The contents of the analysis process and the aspects of the analysis maps may be the same as those of the ophthalmic imaging apparatus 1 described above. The plurality of analysis maps generated are sent to the controller 310.

The display controller 311 displays the plurality of analysis maps generated by the analyzer 330 over the front image of the subject's eye on the display device 400. The display mode here may be the same as that in the ophthalmic imaging apparatus 1 described above (see FIG. 8A, FIG. 8B, etc.).

According to the present embodiment, unlike the conventional technique of individually acquiring and analyzing data about a plurality of sites of the subject's eye, a plurality of analysis maps can be generated from a single three dimensional data acquired using OCT. Therefore, the risk of an error between the analysis maps and the risk of an error in registration are reduced, and therefore the analysis result can be obtained with high accuracy. Further, according to the present embodiment, a plurality of analysis maps can be displayed over a front image of subject's eyes. This makes it possible for the user to easily grasp the state of the subject's eye over a wide region. In this way, according to the present embodiment, it is possible to present the analysis result of high accuracy over a wide region of the subject's eye in a manner that can be easily grasped.

The ophthalmic information processing apparatus can be constructed as a server in a client-server model. For example, it is possible to provide a cloud server having a function as the ophthalmic information processing apparatus according to embodiments, and to offer a display information providing service to a plurality of clients.

Modification Example

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. A configuration applied can be selected according to a purpose, for example. In addition, the operations, actions and effects described in the present specification as well as obvious operations, actions and effects to persons skilled in the art are achieved according to the configuration applied.

What is claimed is:

1. An ophthalmic imaging apparatus comprising:
a three dimensional data generator that generates three dimensional data by scanning a three dimensional region of a fundus of a subject's eye using optical coherence tomography (OCT);
an analyzer that generates a plurality of analysis maps by analyzing a plurality of pieces of partial three dimensional data in the three dimensional data, the analyzer comprising:
a layer region specifier that specifies a layer region corresponding to a predetermined layer tissue of the fundus by analyzing at least one of the plurality of pieces of partial three dimensional data; and
a layer thickness calculator that calculates thicknesses of the layer region at a plurality of positions,
wherein the analyzer generates an analysis map based on the thicknesses of the layer region at the plurality of positions;
a display controller that displays the plurality of analysis maps over a front image of the subject's eye on a display device, wherein the front image is one of a fundus image acquired by a fundus camera, a fundus scan image acquired by a scanning laser ophthalmoscope, and an OCT front image generated from at least part of three dimensional data of the fundus acquired using OCT; and
a storage in which normal eye data that represents a distribution of allowable range of thickness of the predetermined layer tissue for a normal eye is stored in advance,
wherein the analyzer further comprises a comparator that compares the thicknesses of the layer region at the plurality of positions calculated by the layer thickness calculator with the normal eye data,
wherein the analyzer generates a layer thickness evaluation map as an analysis map based on a comparison result obtained by the comparator,
wherein the three dimensional data generator scans a three dimensional region including both an optic nerve head and a fovea centralis of the fundus to generate the three dimensional data,
wherein the analyzer at least executes an analysis of first partial three dimensional data corresponding to a partial three dimensional region including the optic nerve head to generate a first layer thickness evaluation map, and an analysis of second partial three dimensional data corresponding to a partial three dimensional region including the fovea centralis to generate a second layer thickness evaluation map,
wherein the display controller displays at least the first layer thickness evaluation map and the second layer thickness evaluation map over the front image, and
wherein in a case where the first partial three dimensional data and the second partial three dimensional data partially overlap each other, the display controller displays part of the first layer thickness evaluation map and part of the second layer thickness evaluation map overlapping each other.

2. The ophthalmic imaging apparatus of claim 1, wherein the display controller displays the first layer thickness evaluation map and the second layer thickness evaluation map in such a manner that the part of the second layer thickness evaluation map is displayed over the first layer thickness evaluation map.

3. The ophthalmic imaging apparatus of claim 1, wherein in a case where two or more of the plurality of pieces of partial three dimensional data are partially overlapping one another, the display controller displays two or more analysis maps based on the two or more of the plurality of pieces of partial three dimensional data partially overlapping one another.

4. The ophthalmic imaging apparatus of claim 3, wherein the display controller determines an order of the two or more analysis maps based on two or more sites of the subject's eye corresponding to the two or more of the plurality of pieces of partial three dimensional data, and displays the two or more analysis maps partially overlapping one another according to the order determined.

5. The ophthalmic imaging apparatus of claim 3, wherein
the analyzer at least executes a first analysis process on part of the two or more of the plurality of pieces of partial three dimensional data, and a second analysis process different from the first analysis process on another part thereof, and
the display controller determines an order of the two or more analysis maps based on types of analysis processes executed by the analyzer, and displays the two or more analysis maps partially overlapping one another according to the order determined.

6. The ophthalmic imaging apparatus of claim 1, wherein the display controller displays a grid image based on a unit region of an analysis process executed by the analyzer over at least one of the plurality of analysis maps.

7. An ophthalmic information processing apparatus comprising:
a three dimensional data receiver that receives three dimensional data generated by scanning a three dimensional region of a fundus of subject's eye using optical coherence tomography (OCT);
an analyzer that generates a plurality of analysis maps by analyzing a plurality of pieces of partial three dimensional data in the three dimensional data, the analyzer comprising:
a layer region specifier that specifies a layer region corresponding to a predetermined layer tissue of the fundus by analyzing at least one of the plurality of pieces of partial three dimensional data; and
a layer thickness calculator that calculates thicknesses of the layer region at a plurality of positions,
wherein the analyzer generates an analysis map based on the thicknesses of the layer region at the plurality of positions;
a display controller that displays the plurality of analysis maps over a front image of the subject's eye on a display device, wherein the front image is one of a fundus image acquired by a fundus camera, a fundus scan image acquired by a scanning laser ophthalmoscope, and an OCT front image generated from at least part of three dimensional data of the fundus acquired using OCT; and a storage in which normal eye data that represents a distribution of allowable range of thickness of the predetermined layer tissue for a normal eye is stored in advance,
wherein the analyzer further comprises a comparator that compares the thicknesses of the layer region at the plurality of positions calculated by the layer thickness calculator with the normal eye data,
wherein the analyzer generates a layer thickness evaluation map as an analysis map based on a comparison result obtained by the comparator,
wherein the three dimensional data generator scans a three dimensional region including both an optic nerve head and a fovea centralis of the fundus to generate the three dimensional data,
wherein the analyzer at least executes an analysis of first partial three dimensional data corresponding to a partial three dimensional region including the optic nerve head to generate a first layer thickness evaluation map, and an analysis of second partial three dimensional data corresponding to a partial three dimensional region including the fovea centralis to generate a second layer thickness evaluation map,
wherein the display controller displays at least the first layer thickness evaluation map and the second layer thickness evaluation map over the front image, and
wherein in a case where the first partial three dimensional data and the second partial three dimensional data partially overlap each other, the display controller displays part of the first layer thickness evaluation map and part of the second layer thickness evaluation map overlapping each other.

8. An ophthalmic imaging apparatus comprising:
a three dimensional data generator that generates three dimensional data by scanning a three dimensional region of a fundus of a subject's eye using optical coherence tomography (OCT);
an analyzer that generates a plurality of analysis maps by analyzing a plurality of pieces of partial three dimensional data in the three dimensional data, the analyzer comprising:
a layer region specifier that specifies a layer region corresponding to a predetermined layer tissue of the fundus by analyzing at least one of the plurality of pieces of partial three dimensional data; and
a layer thickness calculator that calculates thicknesses of the layer region at a plurality of positions,
wherein the analyzer generates an analysis map based on the thicknesses of the layer region at the plurality of positions; and
a display controller that displays the plurality of analysis maps over a front image of the subject's eye on a display device,
wherein in a case where two or more of the plurality of pieces of partial three dimensional data are partially overlapping one another, the display controller displays two or more analysis maps based on the two or more of the plurality of pieces of partial three dimensional data partially overlapping one another.

9. An ophthalmic information processing apparatus comprising:
a three dimensional data receiver that receives three dimensional data generated by scanning a three dimensional region of a fundus of a subject's eye using optical coherence tomography (OCT);

an analyzer that generates a plurality of analysis maps by analyzing a plurality of pieces of partial three dimensional data in the three dimensional data, the analyzer comprising:
- a layer region specifier that specifies a layer region corresponding to a predetermined layer tissue of the fundus by analyzing at least one of the plurality of pieces of partial three dimensional data; and
- a layer thickness calculator that calculates thicknesses of the layer region at a plurality of positions,
- wherein the analyzer generates an analysis map based on the thicknesses of the layer region at the plurality of positions; and a display controller that displays the plurality of analysis maps over a front image of the subject's eye on a display device, wherein in a case where two or more of the plurality of pieces of partial three dimensional data are partially overlapping one another, the display controller displays two or more analysis maps based on the two or more of the plurality of pieces of partial three dimensional data partially overlapping one another.

\* \* \* \* \*